(12) United States Patent
Oliver

(10) Patent No.: US 11,992,498 B2
(45) Date of Patent: May 28, 2024

(54) SUBSTITUTED N9-ADENINE DERIVATIVES, PHARMACEUTICAL COMPOSITIONS CONTAINING SAME AND USE THEREOF

(71) Applicant: Iván Silió Oliver, Palma de Mallorca (ES)

(72) Inventor: Iván Silió Oliver, Palma de Mallorca (ES)

( * ) Notice: Subject to any disclaimer, the term of this patent is extended or adjusted under 35 U.S.C. 154(b) by 378 days.

(21) Appl. No.: 17/254,135

(22) PCT Filed: Jun. 27, 2018

(86) PCT No.: PCT/ES2018/070457
§ 371 (c)(1),
(2) Date: Dec. 18, 2020

(87) PCT Pub. No.: WO2020/002718
PCT Pub. Date: Jan. 2, 2020

(65) Prior Publication Data
US 2021/0260081 A1    Aug. 26, 2021

(51) Int. Cl.
*A61K 31/675*    (2006.01)

(52) U.S. Cl.
CPC ................... *A61K 31/675* (2013.01)

(58) Field of Classification Search
CPC . A61K 31/675; A61K 9/2054; C07F 9/65616; C07D 473/34; A61P 17/00
See application file for complete search history.

(56) References Cited

U.S. PATENT DOCUMENTS

2014/0303112 A1    10/2014    Chen et al.

FOREIGN PATENT DOCUMENTS

WO    WO-9623801 A2 *    8/1996    .......... C07F 9/65586
WO    2016087665 A2    6/2016

OTHER PUBLICATIONS

Alexander et al. J. Med. Chem. 1996, 39, pp. 1321-1330. (Year: 1996).*
Jul. 2, 2019 (WO) International Search Report—App. PCT/ES2018/070457.
Jacobsen, M et al, "Efficient N-arylation and N-alkenylation of the five DNA/RNA nucleobases." The Journal of Organic Chemistry 71 24 (2006): 9183-90.

* cited by examiner

*Primary Examiner* — Kara R McMillian
(74) *Attorney, Agent, or Firm* — Darrell G. Mottley

(57) ABSTRACT

The invention provides new substituted N9-adenine derivatives, pharmaceutical compositions containing these derivatives and the use of the new derivatives and the pharmaceutical compositions containing same as AMPK activators, being suitable for the production of drugs for the treatment of disorders and diseases where AMPK activation plays a relevant role.

6 Claims, No Drawings

SUBSTITUTED N9-ADENINE DERIVATIVES, PHARMACEUTICAL COMPOSITIONS CONTAINING SAME AND USE THEREOF

CROSS-REFERENCE TO RELATED APPLICATIONS

This application is a U.S. National Stage of International Application No. PCT/ES2018/070457, filed Jun. 27, 2018, the entire contents of which is incorporated herein by reference in its entirety.

TECHNICAL FIELD OF THE INVENTION

The present invention relates to new substituted N9-adenine derivatives, to pharmaceutical compositions containing these derivatives and to the use of the new derivatives and the pharmaceutical compositions containing same as AMPK (AMP-Activated Protein Kinase) activators. Thus, the derivatives of the invention and the compositions containing same are suitable for the production of drugs intended for to the treatment of disorders and diseases where AMPK activation plays a relevant role.

BACKGROUND OF THE INVENTION

Most of the cellular processes that consume energy are driven by the conversion of ATP to ADP. When a given stress causes this relationship to decrease, the intracellular content of AMP increases, which activates AMPK, for example during exercise, ischaemia and also in diabetes, where, despite having blood glucose, it cannot enter the cell and therefore the cell resents the lack of energy. Once activated, AMPK phosphorylates a large number of proteins causing the deactivation of certain energy-consuming anabolic pathways, such as macromolecule biosynthesis, cell growth and proliferation, while activating ATP-producing pathways such as glycolysis and fatty acid oxidation. This can be through the phosphorylation of enzymes directly involved in the regulation of the corresponding pathways, or through regulating the gene expression of the cell (S. Fragoso et al., "AMPK AND ENERGY HOMEOSTASIS", REB 27(1): 3-8, 2008).

AMPK activation can regulate different processes in the cell. Specifically at the metabolic level, it acts on the metabolism of fatty acids, glucose, and protein synthesis, among others. At the fatty acid metabolism level, AMPK intervenes by increasing the oxidation of lipids and inhibiting their de novo synthesis. The increase in lipid oxidation takes place in part because AMPK increases the levels of PPAR-α, involved in the transcription of genes that encode proteins involved in β-oxidation (Barish G D, et al., 2006. PPAR delta: a dagger in the heart of the metabolic syndrome. J Clin Invest. 116: 590-7). Likewise, it has been reported that AMPK can directly phosphorylate PPAR-α, although the physiological relevance of this phosphorylation is unknown. AMPK also acts by inhibiting the de novo synthesis of fatty acids and lipids at both the transcriptional and post-translational levels. Thus, it acts by decreasing the synthesis of enzymes involved in lipogenesis, through the regulation of the transcription factors SREBP and ChREBP (Kawaguchi T, et al., 2002, Mechanism for fatty acid "sparing" effect on glucose-induced transcription: regulation of carbohydrateresponsive element-binding protein by AMPactivated protein kinase. J Biol Chem. 277: 3829-35). It can also act directly on fatty acid synthesis enzymes. It phosphorylates ACC1 on Ser77 and Ser79, ACC2 on Ser219 and Ser221, and possibly FASN by inhibiting them (An Z, et al., 2007, Nicotine-induced activation of AMP-activated protein kinase inhibits fatty acid synthase in 3T3L1 adipocytes: a role for oxidant stress. J Biol Chem. 282: 26793-801). In this way, a decrease in lipogenesis takes place, as well as an increase in β-oxidation. At the level of glucose metabolism, AMPK acts by increasing glycolysis and inhibiting gluconeogenesis. It has been reported to regulate glycolysis by acting, for example, on GEF, which is involved in the transcription of Glut-4. AMPK phosphorylates GEF in such a way that it increases its affinity for the Glut-4 promoter and increases its level of transcription (Holmes B F, et al., 2005, Regulation of muscle GLUT4 enhancer factor and myocyte enhancer factor 2 by AMP-activated protein kinase. Am J Physiol Endocrinol Metab. 289:E1071-6; Screaton R A, et al., 2004, The CREB coactivator TORC2 functions as a calcium- and cAMPsensitive coincidence detector. Cell. 119: 61-74; Jørgensen S B, et al., 2007, Role of AMPKalpha2 in basal, training-, and AICAR-induced GLUT4 hexokinase II, and mitochondrial protein expression in mouse muscle. Am J Physiol Endocrinol Metab. 292: E331-9). Likewise, AMPK also regulates mitochondrial metabolism, its major effector being the transcription factor PGC1α. AMPK directly phosphorylates and activates this transcription factor which is involved in the transcription of genes involved in oxidative phosphorylation and mitochondrial biogenesis.

The identification of AMPK as an indirect target of well-known anti-diabetic drugs has led in recent years to the increasing development of more effective and specific AMPK activators.

Thus, the search for new AMPK activators has been reflected in numerous investigations, describing drugs considered indirect activators of AMPK, inhibiting the production of mitochondrial ATP and altering the AMP:ATP ratio in the cell, thus influencing the treatment of metabolic disorders (Hawley S A, et al., Use of cells expressing gamma subunit variants to identify diverse mechanisms of AMPK activation. Cell Metab 2010; 11(6):554-65). These include biguanide derivatives (e.g., metformin), thiazolidinediones, and phytochemicals. Direct activators that bind directly to the three subunits (alpha, beta, or gamma) of the AMPK holoenzyme have also been researched.

Thus, for example US20060287356 A1 describes thienopyridone derivatives as direct AMPK activators, in particular activating AMPK via an allosteric mechanism and by inhibiting dephosphorylation in threonine. In this case, the effects on glucose and lipid metabolism observed in mice treated with these derivatives were mainly produced by AMPK stimulation in the liver.

WO2010103040 A1 describes the compound 5-aminoimidazole-4-carboxamide riboside (AICAR) as an activator of AMPK, which is metabolised to ZMP, an AMP analogue, by adenosine kinase (AK). ZMP binds to the AMPK gamma subunit and emulates the effect of AMP on allosteric activation of AMPK kinase, with antidiabetic effects in animal models. However, AICAR has low bioavailability and its effective administration requires high doses of intravenous administration, mainly due to its low gastrointestinal absorption and its rapid conversion into a multitude of metabolites that are not active against AMPK.

In the case of the known active ingredient Metformin, a biguanide derivative, an indirect activator of AMPK as mentioned above, its administration involves the use of high doses of active ingredient and unwanted side effects, such as lactic acidosis.

In view of the foregoing, there is still a need for new AMPK activators useful in the treatment or prevention of AMPK activation-related disorders, such as age-related neoplastic, neurodegenerative or metabolic pathologies, in particular as agonists of the bateman domains (structure formed by two CBS motifs—cystathione-beta-synthase) in tandem of the AMPK gamma subunit.

The compounds of the present invention are designed as AMP mimetics that bind to the nucleotide binding sites of the gamma subunit. AMPK has many downstream targets that affect glucose and glycogen metabolism and lipid and cholesterol biosynthesis that make these compounds good candidates for the treatment and/or prevention of metabolic diseases such as hypercholesterolemia, obesity, type 2 diabetes or metabolic syndrome (also called X syndrome). Thus, the compounds of the present invention are especially suitable for the treatment and/or prevention of this type of disorders at low effective doses, their $EC_{50}$ (maximum effective mean concentration) being much lower than the $EC_{50}$ of the AICAR derivatives or of the biguanide derivatives already known from the state of the art.

DESCRIPTION OF THE INVENTION

According to a first aspect, the invention relates to adenine N9-[aryl, heteroaryl)phosphonate derivatives as AMPK activators of the following general formula (I)

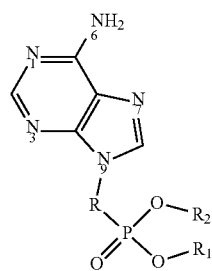

(I)

where
R is a 5 or 6-membered ring aryl group or a 5 or 6-membered ring heteroaryl group, the aryl or heteroaryl being possibly substituted in its free positions with one or more substituents, same or different, selected from deuterium, a halogen atom, —OH, —CH₃, —CN, —OCH₃, OCH₂CH₃, —CH₂COOH, —CH₂COOCH₃, —COOH—COCH₃, —COH.

$R_1$ and $R_2$ are selected, independently from each other, from H, a linear or branched (C1-22) alkyl group, a (C2-22) alkenyl group, a (C2-22)alkynyl group, a (C3-7)cycloalkyl group, a (C3-22)-COOH alkyl group, a (C5-6)-COOH aryl group, an amino acid, preferably alanine, serine or arginine, a glycerol, choline or sphingomyelin group; or they are selected, independently of each another, from alkali metal or alkaline earth metal cations, in particular sodium or magnesium, and can also be a transition metal cation or any acceptable cation;

and where
"aryl group" is a 5 or 6-membered ring aromatic hydrocarbon group, the aryl being possibly unsubstituted or mono or polysubstituted, with the same or different substituents, independently selected from the group consisting of a halogen atom, methyl, ethyl, propyl, isopropyl and cyclopropyl, deuterium and hydroxyl.

"Heteroaryl group" is a 5 or 6-membered ring aromatic hydrocarbon group where at least one of the ring carbons has been replaced by N, O, S, P, or Se.

the phosphonyl group

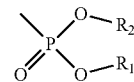

can be linked to any carbon atom of the aryl or heteroaryl ring unsubstituted with another substituent, for example at the ortho, meta or para positions relative to adenine in the case of a 6-membered heteroaryl.

In the context of the present invention, the term alkyl (C1-22), alkenyl (C2-22) or alkynyl (C2-22) group is understood to be aliphatic hydrocarbon groups of 1 to 22 or possibly 2 to 22 carbon atoms, in the case of alkenyls or alkynyls including at least one C=C or CC bond respectively.

Preferred compounds of formula (I) are those where R is an aryl group selected from phenyl or cyclopentadienyl, of the following formulas (Ia-d), $R_1$ and $R_2$ being as defined above:

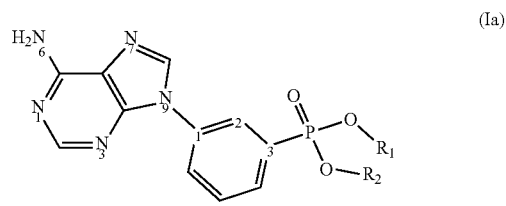
(Ia)

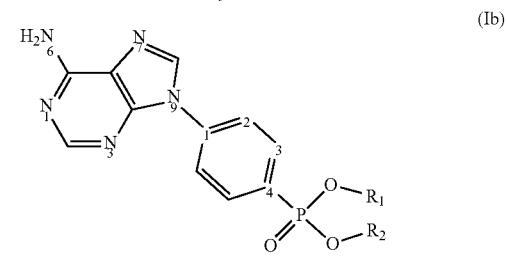
(Ib)

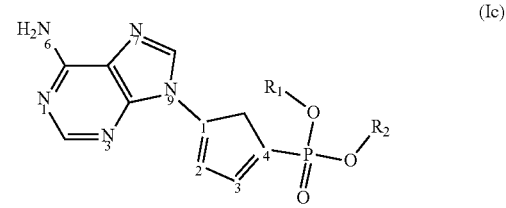
(Ic)

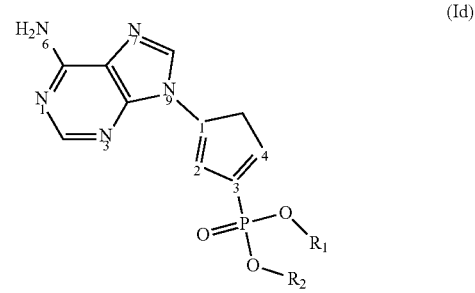
(Id)

Equally preferred are compounds of formula (I) where R is a heteroaryl group selected from among pyridine, pyrimidine, pyrrolyl, pyrazolyl, pyranyl, furanyl, thiophenyl, phospholoyl or selenophenyl, of the following formulas (Ie-p), $R_1$ and $R_2$ being as defined above:

(Ie)
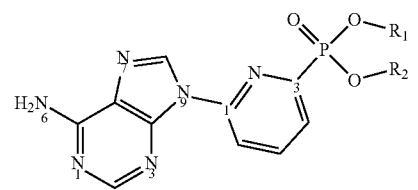

(If)
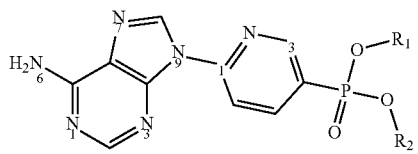

(Ig)
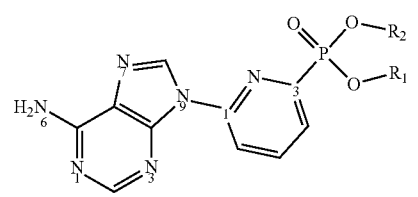

(Ih)
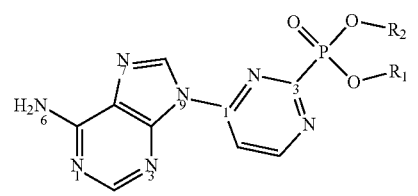

(Ii)
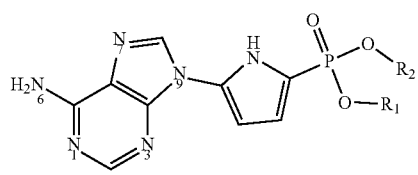

(Ij)
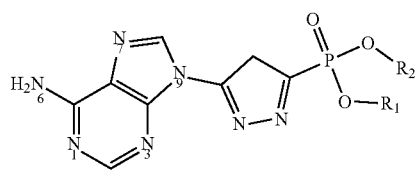

(Ik)
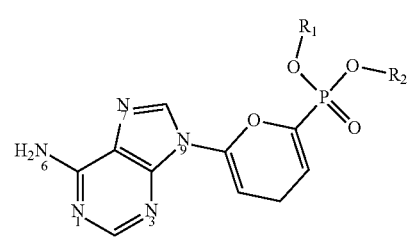

(Il)
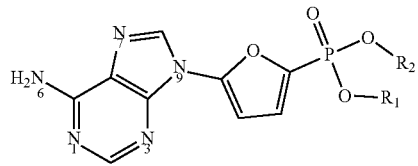

-continued

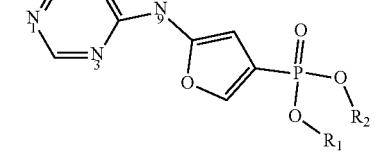

(In)
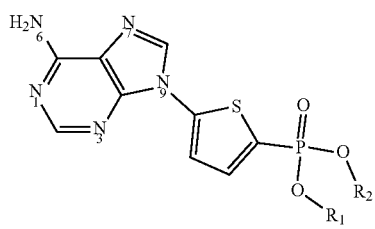

(Io)
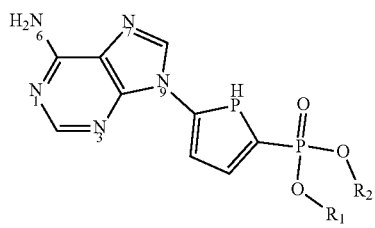

(Ip)
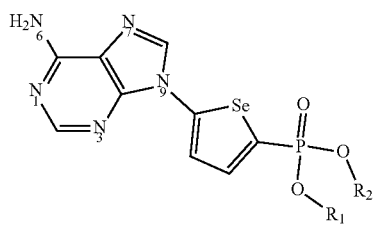

Among the compounds of the invention, those particularly preferred are N9-phenyl-3-phosphonyl-adenine, the particular case of compound (Ia) where $R_1$ and $R_2$ are both hydrogen, N9-(2-furanyl)-5-phosphonyl-adenine, the particular case of compounds (Il) and (Im) where $R_1$ and $R_2$ are both hydrogen and N9-(3-diethylphosphonyl)phenyl-adenine, the particular case of compound (Ia) where $R_1$ and $R_2$ are both an ethyl group.

The invention also relates to pharmaceutical compositions containing the above-described compounds in a therapeutically effective amount in combination with one or several pharmaceutically acceptable excipients, as well as to the use of said pharmaceutical compositions for the production of drugs useful for the treatment and/or the prevention of disorders and diseases where AMPK activation plays a relevant role, for example in metabolic diseases such as hypercholesterolemia, obesity, type 2 diabetes or metabolic syndrome (also called syndrome X), but also for musculoskeletal function, endocrine function, cellular homeostasis, adaptation to environmental stress, as well as for the treatment or prevention of dermatological pathologies that can be controlled and/or reversed by AMPK holoenzyme activation.

Among the pharmaceutical compositions according to the invention, particularly noted are those suitable for oral, parenteral, intramuscular and intravenous, per or transcutaneous, nasal, rectal, perlingual, ocular, respiratory administration, and more specifically those in the form of simple tablets, sublingual tablets, hard capsules, perlingual tablets, capsules, lozenges, injections, sprays, suppositories, dermal creams, ointments or gels.

In a preferred embodiment, the compositions of the invention are administered orally.

In addition to the compounds of the invention, the pharmaceutical compositions according to the invention contain one or more excipients or carriers selected from diluents, lubricants, binders, disintegrators, stabilizers, preservatives, absorbents, colorants, sweeteners, flavourings, etc., these excipients being selected based on the final dosage form of the pharmaceutical composition.

As a non-limiting example, the following can be cited:
- as diluents: lactose, dextrose, sucrose, mannitol, sorbitol, microcrystalline cellulose, glycerin;
- as lubricants: silica, talc, stearic acid and its magnesium and calcium salts, polyethylene glycol;
- as binders: magnesium aluminum silicate, starch, gelatin, gum tragacanth, methylcellulose, sodium carboxymethylcellulose and polyvinylpyrrolidone;
- as disintegrants: agar, alginic acid and its sodium salt, effervescent mixtures;
- as solubilisers: cyclodextrins, polyvinylcaprolactam, polyvinyl acetate and polyethylene glycol.

The useful dosage varies according to the sex, age and weight of the patient, the route of administration, the nature of the disorder and any associated treatments, ranging between 1 µg and 1,000 mg of a compound according to the invention per kg of body weight of the subject to be treated, preferably between 1 mg and 300 mg per kg of body weight, in one or more doses per day.

In the context of the invention, the subject to be treated is a human or animal mammalian subject.

For example, in the case of a pharmaceutical composition according to the invention that includes the adenine derivative N9-(3-diethylphosphonyl)phenyl-adenine, the particular case of the compounds of formula (I) where R is a phenyl group and $R_1$ and $R_2$ are both an ethyl group, in particulate form together with the appropriate excipients, compressed into a tablet or filled in a capsule, for oral administration, said compound of the invention is administered at the aforementioned dose, the compound of the invention being released via acid hydrolysis in the acidic pH of the stomach, in addition to being absorbed by the prodrug and being activated intracellularly via esterase enzymes and extracellularly in the small intestine, as well as by hydrolysis in a physiological aqueous medium, although to a lesser extent.

In another example of a pharmaceutical composition for topical administration in the form of an ointment, for example for the treatment of dermatological pathologies that can be controlled and/or reversed by AMPK holoenzyme activation, the compounds of the invention are included in said pharmaceutical composition in a weight concentration range of 0.1 mg/g of ointment to 2.0 mg/g of ointment, the pharmaceutical composition including as suitable excipients cetyl alcohol, distilled water, glycerol stearate, liquid paraffin, polysorbate 60, polysorbate 80, propylene glycol and sodium ascorbate. In another example of a pharmaceutical composition for topical administration, the compound of the invention would be dissolved in a mixture of polyethylene glycol 300, 1500 and 4000 and sodium ascorbate.

Contemplated as dermatological pathologies that can be controlled and/or reversed by AMPK holoenzyme activation in the present invention are, for example, Xeroderma pigmentosum and skin cancer, including but not limited to melanoma and basal cell carcinoma, (Wu, C L et al., Role of AMPK in UVB-induced DNA damage repair and growth control. Oncogene 32, 2682-9 (2013)).

Examples

In the following examples, which further illustrate the invention and should not be construed as limiting thereof, a synthesis procedure of an example of a preferred embodiment of the compound of formula (I), in particular N9-(3-diethylphosphonyl)phenyl-adenine, is described, the particular case of the compounds of formula (I) where R is a phenyl group and $R_1$ and $R_2$ are both an ethyl group.

General Synthesis of the Compounds of Formula (I)

The general synthesis mechanism is governed by a Chan-Lam coupling mediated by a copper(II) salt in stoichiometric amounts between neutral adenine and a halo-aryl boronic acid, for example 3-bromophenylboronic acid or 4-bromophenylboronic acid, as described in Yue, Y., et al., Copper-catalyzed cross-coupling reactions of nucleobases with arylboronic acids: An efficient access to N-arylnucleobases, European J. Org. Chem. 5154-5157 (2005). To the coupling product purified by column chromatography, for example 9-(3-bromophenyl)adenine and 9-(4-bromophenyl)adenine, a dialkylphosphine is coupled under conditions similar to Negishi coupling with tetrakis(trifefilphosphine)-palladium (0) as the catalyst, triethylamine as the base and anhydrous dimethylformamide as the solvent. Subsequently, the two ester bonds of the phosphonate can be hydrolysed in an acid medium with aqueous hydrochloric acid to obtain the corresponding phosphonic acid derivative and in turn subsequently be converted into a salt, for example disodium, making it react with sodium hydroxide in an aqueous medium.

Alternatively, 6-chloropurine and the corresponding halo-heteroaryl boronic acid is the basis used to generate non-benzylic heteroaryl derivatives, as described in Morellato, L., et al., Synthesis of novel 9-aryl and heteroarylpurine derivatives via copper mediated coupling reaction, Tetrahedron Lett (2014) and the desired dialkylphosphine is then coupled under conditions similar to Negishi coupling with tetrakis(trifefilphosphine)-palladium(0) as catalyst, triethylamine as base and anhydrous dimethylformamide as solvent.

Synthesis of N9-(3-diethylphosphonyl)phenyl-adenine

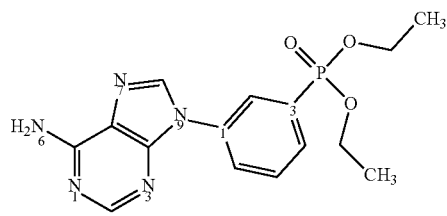

Compound N9-(3-diethylphosphonyl)phenyl-adenine is obtained from adenine following a two-step process:

Step 1: 3-bromophenyl-N9-adenine

This stage is adapted from Yue, Y., et al., Copper-catalyzed cross-coupling reactions of nucleobases with arylboronic acids: An efficient access to N-arylnucleobases, European J. Org. Chem. 5154-5157 (2005).

Briefly, 5 mmol of adenine was added to 500 ml of a 4:1 methanol-water mixture containing 5 mmol of copper(II) acetate monohydrate, 10 mmol of N,N,N',N'-tetramethylethylenediamine and 10 mmol of 3-bromophenyl-boric acid. The mixture was stirred under an air atmosphere for one hour at room temperature in a 1 L flask. Methanol was added to the solution in the flask, the mixture was filtered through celite, and the solvents were evaporated. The resulting solid was purified by flash chromatography using silica gel and a load of $CH_2Cl_2$:MeOH 20:1 and $CH_2Cl_2$:MeOH 10:1 as eluent. The title product with r=0.25 was obtained as a white crystalline solid. Yield 50%. Purity >98%.

Stage 2: N9-(3-diethylphosphonyl)phenyl-adenine 2 mmol of 3-bromophenyl-N9-adenine, 3 mmol of triethylamine, 0.1 mmol of tetrakis(trifefilphosphine)palladium (0) and 3 mmol of diethyl phosphite were loaded into a 50 ml round flask. Then 10 ml of anhydrous dimethylformamide was added and the mixture was stirred for one hour at 100° C. The dimethylformamide was evaporated and the solid obtained was purified by chromatography using silica gel and $CH_2Cl_2$:MeOH 10:1 as eluent. The desired product N9-(3-diethylphosphonyl)phenyl-adenine with r=0.20 was obtained as a white/beige crystalline solid. Yield 90%. Purity >98%. Melting point 104° C.

Spectroscopic Analysis:

IR (KBr), $cm^{-1}$: 3297 ms, 3102 ms, 1676 s, 1599 s, 1487 ms, 1307 s, 1050 ms, 1022 s, 656 m, 562 m. (ms=medium-strong, s=strong, m=medium)

$^1$H-NMR (300 MHz, dmso-d6): δ (ppm)=8.67 s (1H, $H8_{adenine}$), 8.30 dd (1H, H1, $J_{PH}$=16.6 Hz, $J_m$=1.2 Hz), 8.23 s (1H$2_{ade}$ CH), 8.17-8.14 m (1H, H2), 7.79-7.75 m (2H, H3+H4), 7.43 bs (2H, NH2), 4.08 dq (4H, CH2, JP-H=15.3 Hz, JH-H=7.2 Hz), 1.29-1.25 t (6H CH3, JH-H=7.2 Hz) ppm. HRMS (ESI) $[M+H]^+$ $[C_{15}H_{18}N_5PO_3+H]^+$: calculated m/z=348.1218; found m/z=348.1220.

AMPK Activation Assay

C2C12 cells from the mouse muscle myoblastoma cell line (from Sigma-Aldrich) were seeded at a cell density of 10,000 cells per well in a 96-well plate in 200 μl of growth medium (high glucose DMEM, 10% foetal bovine serum (PBS), penicillin and streptavidin). The cells were allowed to grow until confluence and on the day of the assay they were incubated with the compound of interest in 100 μl of growth medium at 37° C. and 5% $CO_2$ in an incubator for between 1 and 24 hours. All conditions were tested in quadruplicate. The compounds were administered dissolved in sterile anhydrous dimethyl sulphoxide at different concentrations. As a positive control for AMPK activation, an adenosine monophosphate (AMP) solution with a final concentration of 100 μl was used. After the corresponding times, the medium was removed and the cells were carefully washed three times with PBS at room temperature and the Abcam Elisa kit was used to quantify the ratio of phosphorylated α-AMPK:total α-AMPK. The manufacturer's instructions were followed and the signal was quantified using a Licor Odissey® scanner. Compound N9-(3-diethylphosphonyl)phenyl-adenine exhibited higher AMPK activity than the AMP positive control at concentrations as low as 30 nanomolar after 4 hours of incubation.

Specifically, the compound N9-(3-diethylphosphonyl) phenyl-adenine demonstrated an AMPK activity greater than 500% of that obtained with the AMP positive control at concentrations as low as 30 nanomolar after 4 hours of incubation. Those compounds with an EC50 lower than 1 micromolar and activation with respect to the AMP control higher than 80% are considered desired active compounds. The compounds selected as AMPK activators according to the criteria described above are used in glucose consumption tests and MTT cell viability tests.

Glucose Consumption Test

C2C12 cells of the mouse muscle myoblastoma cell line (from Sigma-Aldrich) were seeded at a cell density of 10,000 cells per well in a white 96-well plate compatible with the use of a luminometer. Cells were grown for 5 days in 200 μl/well of growth medium (high glucose DMEM, 10% foetal bovine serum (PBS), penicillin and streptavidin) in an incubator at 37° C. and 5% $CO_2$. The medium was changed every two days. The medium was then replaced with a differentiation medium (low glucose DMEM, 2% N-hydroxysuccinimide, penicillin and streptavidin), allowing the cells to differentiate into myotubes for three days. The medium was changed every day. One day prior to testing, cells were serum starved (low glucose DMEM, penicillin and streptavidin). The medium was then replaced by a DMEM medium without glucose and the compound N9-(3-diethylphosphonyl)phenyl-adenine was incubated for one hour at different concentrations, replicating the conditions in quadruplicate. The positive control consisted of 100 nanomolar human insulin solution (from Sigma). A Promega glucose consumption kit was used following the manufacturer's instructions. The kit is based on the intracellular uptake of 2-deoxyglucose as a chemical analogue of glucose, coupled to a luciferin luminometric enzyme assay, in relation to the fact that the results obtained are proportional to the intracellular concentration of said glucose analogue.

Total luminescence was measured on a Biotek MX luminometric plate reader. The compound N9-(3-diethylphosphonyl)phenyl-adenine exhibited glucose consumption activity analogous to or greater than that of insulin controls at concentrations as low as 30 nanomolar. Luminosity as % of the control for N9-(3-diethylphosphonyl)phenyl-adenine (30 nanomolar): 125±9%.

MTT Cell Viability/Proliferation Assay

The MTT redox assay is based on the metabolic reduction of bromide from 3-(4,5-dimethylthiazol-2-yl)-2,5-diphenyltetrazole (MTT) that is produced by the mitochondrial enzyme succinate-dehydrogenase, which colours the formazan dye blue, allowing to determine the mitochondrial functionality of the treated cells.

C2C12 cells were seeded at a density of 10,000 cells per well in a white 96-well plate compatible with the use of a luminometer. Cells were grown for 5 days in 200 μl/well of growth medium (high glucose DMEM, 10% FBS, penicillin and streptavidin), with the medium being replaced every two days. Subsequently, the medium was replaced by a differentiation medium (low glucose DMEM, 2% NHS, penicillin and streptavidin) and the cells were allowed to differentiate in myotubes for three days, the medium being changed every day. In all processes, cells were incubated at 37° C. and 5% $CO_2$ in a cell incubator. The compound N9-(3-diethylphosphonyl)phenyl-adenine was incubated for 24 and 48 hours in low glucose DMEM without serum. The concentrations of the incubated compound ranged from 10 nanomolar to 1 millimolar. As a positive control for AMP activation, an AMP solution with a final concentration of 100 μl was used. After incubation, 10 μl of the MTT reagent (Abcam) was added to each well and, after 30 min, 45 min and 60 min of incubation, the absorbance at 490 nm was measured in a photometer with a Biotek TX plate reader. The reading is an indirect measure of the NAD(P)H enzyme dependent on cellular oxidase reductases.

The compound N9-(3-diethylphosphonyl)phenyl-adenine showed a significantly higher signal compared to controls at nanomolar concentrations. Luminosity as % of the control for N9-(3-diethylphosphonyl)phenyl-adenine (30 nanomolar and 48 hours incubation): 157±5%.

Example of a Pharmaceutical Composition According to the Invention

An example of a pharmaceutical composition for the formulation of a drug in a daily oral dose for a human adult includes 20 mg of a compound according to the invention in compressed particulate form together with the following excipients: microcrystalline cellulose, sodium carboxymethyl starch type A (derived from potato), anhydrous colloidal silica and magnesium stearate.

The invention claimed is:

1. AMPK activator substituted N9-adenine derivatives having the following general formula (I)

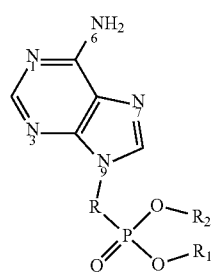

(I)

wherein,

R is a phenyl group;

R1 and R2 are both ethyl groups;

which is N9-(3-diethylphosphonyl)phenyl-adenine.

2. Pharmaceutical compositions containing at least one compound according to claim 1 in combination with one or several pharmaceutically acceptable excipients.

3. Pharmaceutical compositions according to claim 2, wherein the compound is present in an effective dose of between 1 μg and 1,000 mg of the compound per kg of body weight of the subject to be treated.

4. Pharmaceutical compositions according to claim 3, wherein the compound is present in an effective dose of between 1 mg and 300 mg per kg of body weight.

5. A method of treating or preventing an AMPK activation-related disorder or disease in a subject comprising administering the pharmaceutical composition of claim 2 to a subject in need thereof.

6. The method according to claim 5, wherein the AMPK activation-related disorder or disease is selected from a metabolic disease, a dermatological pathology disease, hypercholesterolemia, obesity, type 2 diabetes or metabolic syndrome, for musculoskeletal function diseases, endocrine function diseases, cellular homeostasis disease or disorders, adaptation to environmental stress.

* * * * *